United States Patent
Cage

(10) Patent No.: US 8,900,161 B2
(45) Date of Patent: Dec. 2, 2014

(54) TISSUE SAMPLING DEVICE AND METHOD

(75) Inventor: Logan Cage, Bloomington, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 293 days.

(21) Appl. No.: 13/366,881

(22) Filed: Feb. 6, 2012

(65) Prior Publication Data

US 2012/0253229 A1  Oct. 4, 2012

Related U.S. Application Data

(60) Provisional application No. 61/470,692, filed on Apr. 1, 2011.

(51) Int. Cl.
*A61B 10/02* (2006.01)
*A61B 17/32* (2006.01)
*A61B 17/3205* (2006.01)
*A61B 18/08* (2006.01)

(52) U.S. Cl.
CPC ....... *A61B 10/0266* (2013.01); *A61B 17/32053* (2013.01); *A61B 18/082* (2013.01); *A61B 17/32056* (2013.01)
USPC .............................. 600/567; 606/170; 606/184

(58) Field of Classification Search
CPC ........... A61B 10/0266; A61B 2010/02; A61B 2010/0208; A61B 10/02
USPC ........................... 600/567, 566; 606/170, 184
See application file for complete search history.

(56) References Cited

U.S. PATENT DOCUMENTS

| | | |
|---|---|---|
| 4,461,305 A | 7/1984 | Cibley |
| 5,211,651 A | 5/1993 | Reger et al. |
| 5,397,320 A | 3/1995 | Essig et al. |
| 5,687,739 A | 11/1997 | McPherson et al. |
| 6,152,932 A | 11/2000 | Ternström |
| 6,156,043 A | 12/2000 | Krahn |
| 6,190,394 B1 | 2/2001 | Lind et al. |
| 6,589,240 B2 | 7/2003 | Hinchliffe |
| 6,626,903 B2 | 9/2003 | McGuckin, Jr. et al. |
| 7,963,928 B2* | 6/2011 | Krause .................. 600/562 |
| 2009/0182324 A1* | 7/2009 | Kurtulus ................ 606/37 |
| 2009/0227895 A1* | 9/2009 | Goldenberg ........... 600/567 |

* cited by examiner

*Primary Examiner* — Max Hindenburg
*Assistant Examiner* — John Pani
(74) *Attorney, Agent, or Firm* — Liell & McNeil

(57) ABSTRACT

A tissue sampling device includes a cannula having an elongate tubular body with a sharpened coring tip. A shaft extends within the cannula and is coupled with a cutter having an axially advancing wire extending between a distal end of the shaft and the sharpened coring tip. The axially advancing wire is movable in a cutting path defining an arc about the longitudinal axis, by way of rotating the shaft relative to the cannula.

16 Claims, 5 Drawing Sheets

TISSUE SAMPLING DEVICE AND METHOD

RELATION TO OTHER PATENT APPLICATION

This application claims priority to provisional patent application 61/470,692, filed Apr. 1, 2011 with the same title.

TECHNICAL FIELD

The present disclosure relates generally to devices and methods for obtaining tissue samples for biopsy, and relates more particularly to a tissue sampling device in which a cutter having an axially advancing orientation sweeps an arcing cutting path through body tissue received within a cannula.

BACKGROUND

Acquiring samples of human body tissue for biopsy purposes is performed with a wide variety of devices and methodologies. In many cases, the type of tissue to be sampled can influence the selection of appropriate tools. For instance, tissue sampling mechanisms used for sampling bone marrow may be quite different from those used in obtaining samples of tissue from the esophagus, or those used to obtain samples from certain internal organs.

While certain tissues can be sampled with a simple needle, others may be best obtained by more sophisticated mechanisms such as movable cutting blades, wires, retrieval baskets. Certain devices employ electro-cauterization to assist in detaching samples of body tissue, reducing the mechanical force needed to cut through body tissue, and reducing trauma to the patient. While many known tissue sampling techniques have found clinical and commercial applications, there is room for improvement. Many devices, while sophisticated, are costly and complex. It may be desirable to use a tissue sampling device only a single time, and substantial costs for a single-use, sophisticated cutting tool may be passed on to the patient or absorbed by the provider. Other problems with conventional technology relate to trauma experienced by the patient, or only narrow practicable use of certain devices with respect to tissue type or sample size.

SUMMARY OF THE DISCLOSURE

In one aspect, a tissue sampling device includes a cannula having an elongate tubular body defining a longitudinal axis extending between a proximal cannula end and a distal cannula end having a sharpened coring tip. The tissue sampling device further includes a shaft having a proximal shaft end, a distal shaft end, and being rotatably positioned within the cannula such that the distal shaft end is recessed from the sharpened coring tip. The tissue sampling device further includes a cutter having an axially advancing orientation and extending within the cannula between the distal shaft end and the sharpened coring tip, the cutter being movable in a cutting path defining an arc about the longitudinal axis, responsive to rotating the shaft relative to the cannula, to detach a piece of body tissue positioned within the cannula between the distal shaft end and the sharpened coring tip.

In another aspect, a method of obtaining body tissue from a patient includes receiving the body tissue within a cannula at least in part by advancing a sharpened coring tip of the cannula into a body tissue mass within the patient. The method further includes detaching a piece of the body tissue from the mass via sweeping a cutter having an axially advancing orientation in an arcing cutting path through the body tissue within the cannula.

In still another aspect, a tissue sampling device includes a cannula defining a longitudinal axis, and having a sharpened coring tip, and a shaft rotatably positioned within the cannula and recessed from the sharpened coring tip. The tissue sampling device further includes a cutter positioned within the cannula and having a plurality of axially advancing cutting wires extending within the cannula between the shaft and the sharpened coring tip. The cutter includes a tissue admission configuration at which the axially advancing cutting wires each include a linear shape, an actuated configuration at which the axially advancing cutting wires each include a curved shape, and switching from the tissue admission configuration to the actuated configuration responsive to rotating the shaft relative to the cannula.

DETAILED DESCRIPTION

Figure 1:
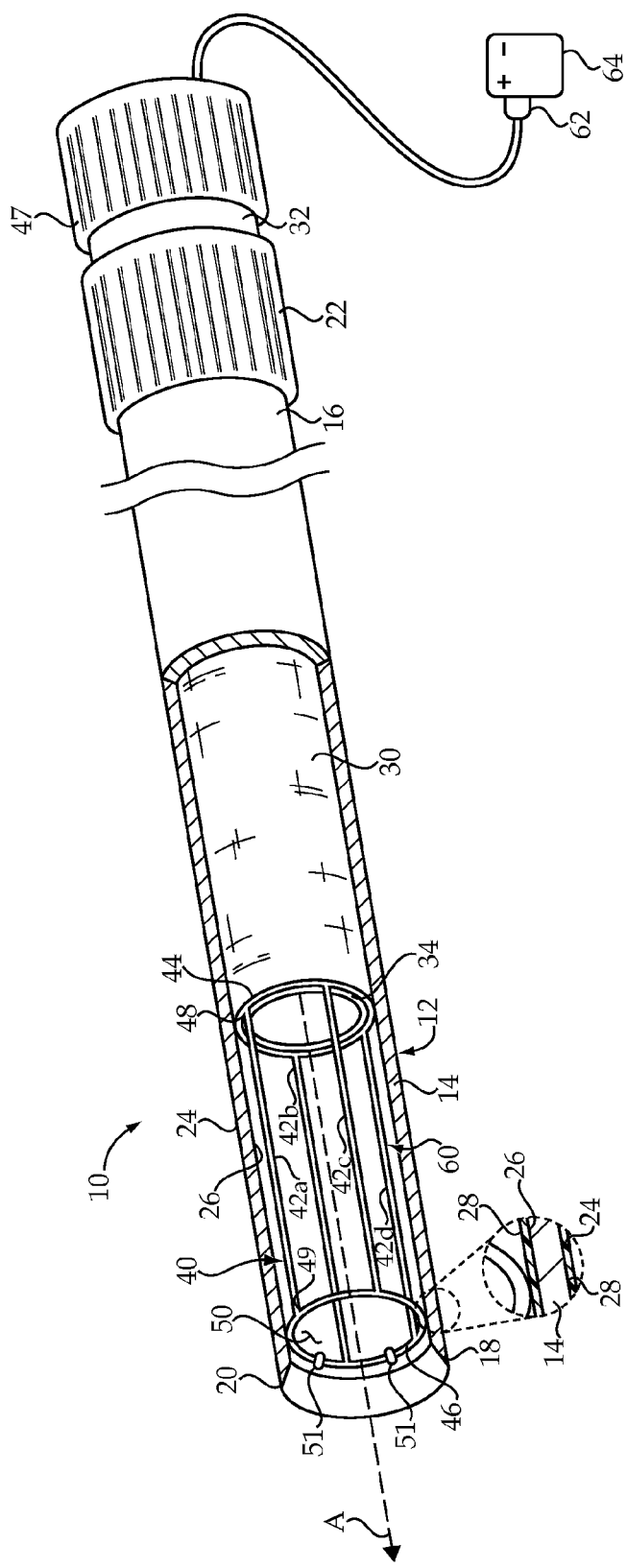
FIG. 1 is a partially sectioned diagrammatic view, including a detailed enlargement, of a tissue sampling device according to one embodiment.

Referring to FIG. 1, there is shown a tissue sampling device 10 according to one embodiment. Device 10 may include a cannula 12 having an elongate tubular body 14 defining a longitudinal axis A extending between a proximal cannula end 16 and a distal cannula end 18. A handle 22 may be coupled with proximal cannula end 16. Distal cannula end 18 may include a sharpened coring tip 20. An elongate shaft 30 is positioned within cannula 12 and may be oriented coaxially with elongate tubular body 14. Shaft 30 may include a proximal shaft end 32 having a handle 47 coupled therewith, and a distal shaft end 34 positioned such that it is recessed within elongate tubular body 14 from tip 20. A cavity 50 extends between sharpened coring tip 20 and distal shaft end 34.

A cutting mechanism or "cutter" 40 having an axially advancing orientation is positioned within cannula 12, and extends between distal shaft end 34 and tip 20. Cutter 40 may include a plurality of axially advancing cutting wires. In certain embodiments, only one cutting wire might be used. Further, rather than cutting wires, a different type of cutter such as an elongate blade might be used. Versions are also contemplated in which struts or the like, comprising elongate, thin strips of material formed integrally with shaft 30, or machined from a cylindrical blank which also comprises shaft 30, are used. In the case of cutting wires, struts, and blades, any suitable cross-sectional shape might be used, such as a cylindrical or angular shape, and/or having serrations. Axially advancing wires 42a-d are each movable in a cutting path, each cutting path defining an arc about longitudinal axis A, responsive to rotating shaft 30 relative to cannula 12. Such relative rotation may be achieved by rotating one of handles 22 and 47 while holding the other stationary, or by simultaneously rotating both handles. In the embodiment shown in FIG. 1, device 10 includes a total of four axially advancing wires 42a-d. Wires 42a-d are arranged in parallel with one another, and also extend parallel longitudinal axis A. It may be noted that wires 42a-d are spaced at equal radial distances from longitudinal axis A, such that wires 42a-d together define a cylinder coaxial with cannula 12. Wires 42a-d may be equally spaced from one another about longitudinal axis A, in other words equally spaced circumferentially about axis A; however, the present disclosure is not thereby limited and non-uniformly spaced wires might be used in other embodiments. Non-parallel wires might also be used. While a total of four wires provide a practical implementation strategy, in other embodiments a different number of wires might be used such as a number from two to five. Even a single wire design may fall within the scope of the present disclosure, as will be further apparent from the following description. Wires 42a-d may each have a thickness less than about 20 thousandths inches, and in one practical implementation strategy a thickness of about 10 thousandths inches.

As mentioned above, shaft 30 may be rotatable relative to cannula 12. In the embodiment shown, cutter 40 is in a tissue admission configuration at which each of wires 42a-d includes a linear shape, and cavity 50 is relatively unobstructed such that tissue may be readily received within cannula 12. Cutter 40 may be adjustable to a second configuration at which wires 42a-d are twisted about one another within cavity 50, assuming curved shapes, responsive to rotating shaft 30 relative to cannula 12. This general principle of rotating shaft 30 relative to cannula 12 and responsively twisting wires 42a-d about one another can be used to cut a sample of tissue from a tissue mass within a patient, as further described herein.

To enable twisting of wires 42a-d about one another, a first wire end 48 of each of wires 42a-d is coupled to distal shaft end 44, and a second wire end 49 of each of wires 42a-d is coupled to distal cannula end 18, such that rotating shaft 30 relative to cannula 12 may cause the corresponding first wire end 48 of each of wires 42a-d to rotate about longitudinal axis A while the opposite corresponding second wire end 49 is held stationary. In FIG. 1, attachments 51, which may include a non-conductive adhesive or a non-conductive weld material for reasons which will be apparent from the following description, attaches a distal hoop 46 of cutting mechanism 40 to distal cannula end 18. A similar attachment mechanism or an alternative coupling strategy altogether may be used to attach a proximal hoop 44 of cutting mechanism 40 to distal shaft end 34. Were hoop 44 to be welded to distal shaft end 34, non-conductive weld material might be unnecessary, or even disfavored, for reasons which will also be apparent from the following description.

Device 10 may cut a tissue sample from a tissue mass within a patient with the assistance of electro-cauterization. To this end, each of wires 42a-d may include a segment of an electrical circuit 60 which is energized by way of connecting an electrical connector 62, electrically connected to shaft 30 and thus electrically connected to cutter 40, with an electrical power source 64. Energization of cutter 40 such that wires 42a-d may be used to cut tissue via electro-cauterization may take place in a conventional manner. As will be readily apparent to those skilled in the art, it may be desirable to electrically insulate cannula 12, and in particular portions of elongate tubular body 14 which contact cutter 40, such that electrical current does not substantially flow between cutting mechanism 40 and cannula 12. In FIG. 1, a detailed enlargement shows a portion of cannula 12, and in particular an electrically insulative coating 28 on an inner surface 26, and also on an outer surface 24 of elongate tubular body 14. Certain electrically insulative materials, such as fluoropolymers, may also provide a relatively low friction surface. Thus, while it may not be strictly necessary to coat outer surface 24 with coating 28, such may be desirable to facilitate sliding device 12 through body tissue during obtaining a sample, as further discussed herein.

As noted above, each of wires 42a-d may be movable in a cutting path within cavity 50, each cutting path defining an arc about longitudinal axis A. The cutting paths defined by wires 42a-d may be different from one another, but may overlap and/or intersect in such a way that each of wires 42a-d cuts part of the way through a core of tissue received within cannula 12. Leveraging the ability to cut part way through a core of tissue with each one of wires 42a-d to detach a sample of tissue from a body tissue mass in a patient can, among other things, make it relatively easy and straightforward to obtain a sizable sample of body tissue quickly and easily, and without undue trauma to the patient. Sample size of tissue cut from a patient might be between about 100 $mm^3$ and about 1000 $mm^3$, however the present disclosure is not thereby limited.

Figure 2B:
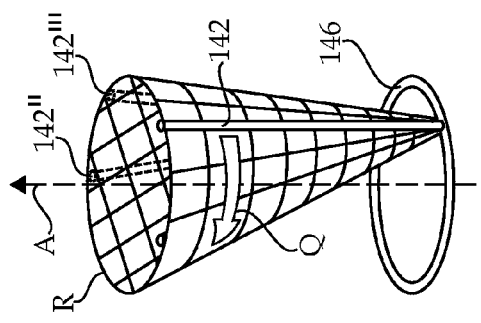
FIG. 2b is a diagrammatic view of a portion of the cutting mechanism of FIG. 2a graphically illustrating an arcing cutting path about an axis.
Figure 2A:
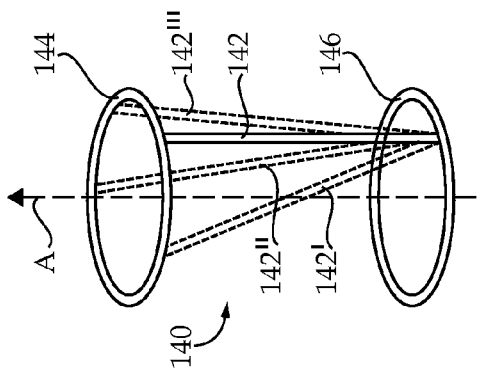
FIG. 2a is diagrammatic view of a cutting mechanism according to one embodiment.

Turning now to FIG. 2a, there is shown a diagrammatic view of a cutting mechanism 140 according to an embodiment having certain similarities with cutting mechanism/cutter 40, but certain differences. Mechanism 140 includes a single axially advancing wire 142 extending between a proximal hoop 144 and a distal hoop 146. Mechanism 140 could be used in place of mechanism 40 in the embodiment of FIG. 1, but will have a tendency to cut a sample of tissue in a slightly different manner. In particular, rather than multiple wires having multiple different cutting paths which intersect and/or overlap with one another, wire 142 defines the sole cutting path. In the embodiment of FIG. 2a, hoop 144 might be rotated in either of a clockwise or a counterclockwise direction about longitudinal axis A relative to distal hoop 146. Rotation of proximal hoop 144 will impart a tendency for wire 142 to sweep through a cutting path defining an arc about longitudinal axis A, and further defining a 3-dimensional shape. A first, a second, and a third illustrative position of wire 142 as it might appear upon being swept in a clockwise direction about its cutting path are shown via reference numerals 142', 142'', and 142'''. Referring also to FIG. 2b, there is shown an illustration of a cone R which corresponds to a 3-dimensional shape which might be defined by the cutting path of wire 142. Proximal hoop 144 is not shown in FIG. 2b. Thus, in at least certain embodiments a 3-dimensional shape defined by the cutting path of an axially advancing wire may be understood as a conoidal shape. A cut sample of body tissue using cutting mechanism 140 might have a shape similar to cone R. It may also be noted from FIG. 2b by way of an arrow Q that an arc about longitudinal axis A defined by the cutting path of wire 142 may lie on the surface of the conoidal shape illustrated via cone R. When a cutting mechanism such as cutting mechanism 140 is used in obtaining a tissue sample, the shape of the tissue sample could be expected to be at least roughly conoidal, as determined by the cutting path of wire 142.

Figure 3C:
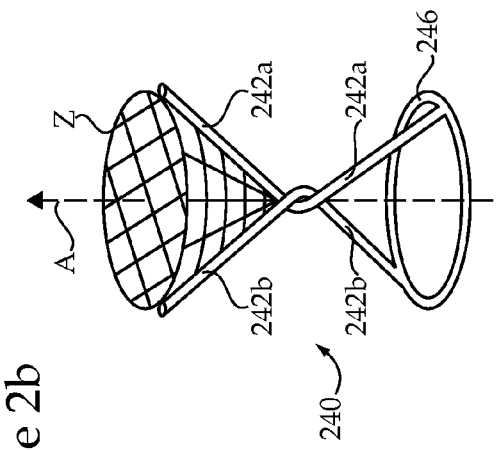
FIG. 3c is a diagrammatic view of a portion of the cutting mechanism of FIGS. 3a and 3b, having been further advanced through the cutting path and graphically illustrating the cutting path.

The example shown in FIGS. 2a and 2b represents a case where sweeping a cutting wire 360° about longitudinal axis A might be expected to define a 3-dimensional shape which is actually a cone. In multi-wire embodiments, the cutting paths defined by each of the wires can be expected to intersect and/or overlap with one another. In multi-wire embodiments, the respective cutting paths may still be understood as conoidal, even though the twisting of the multiple wires about one another could be expected to prevent any individual wire from actually traversing a cutting path defining a true cone. Referring now to FIG. 3a, there is shown a cutting mechanism 240 according to an embodiment in which a total of two axially advancing wires 242a and 242b are used, each of wires 242a and 242b extending between a proximal hoop 244 and a distal hoop 246. Rotating hoop 244 relative to hoop 246 can be expected to sweep cutting wires 242a and 242b through cutting paths which start out as generally conoidal similar to the embodiment of FIGS. 2a and 2b, but whose cutting paths intersect when wires 242a and 242b contact such that a tissue sample having a shape differing somewhat from that obtained with the embodiment of FIGS. 2a and 2b is ultimately cut from a mass of body tissue.

Figure 3B:
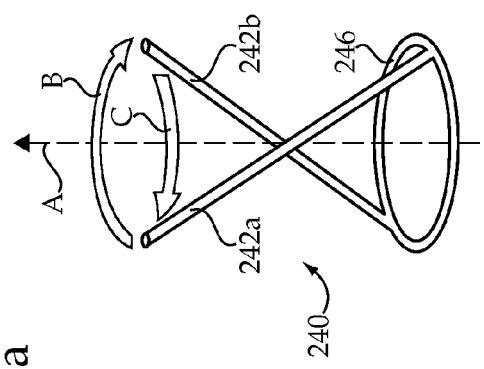
FIG. 3b is a diagrammatic view of a portion of the cutting mechanism of FIG. 3a, having been advanced through a cutting path.
Figure 3A:
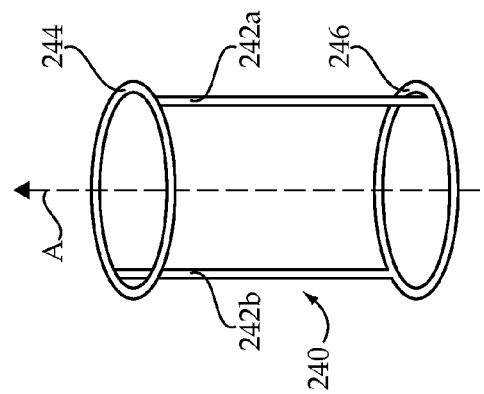
FIG. 3a is a diagrammatic view of a cutting mechanism according to another embodiment.

Referring also to FIG. 3b, there is shown mechanism 240 where proximal hoop 244 is not shown, but illustrated as mechanism 240 might appear where hoop 244 has been rotated approximately 180° relative to hoop 246. Wires 242a and 242b have thus been swept approximately through an arc of 180° in their respective cutting paths. Arrow C indicates an approximate path traversed by a proximal tip of wire 242a, whereas arrow B illustrates an approximate path traversed by the proximal tip of wire 242b. Each of wires 242a and 242b could be understood to have swept through their respective cutting paths such that each cutting path has defined one half of a cone, albeit two separate cones. From the state shown in FIG. 3b, wires 242a and 242b may contact one another, and begin to twist about one another approximately at a twist point intersected by axis A. It may also be noted that the cutting paths of wires 242a and 242b intersect within longitudinal axis A.

Turning to FIG. 3c, there is shown cutting mechanism 240 as it might appear where wires 242a and 242b have been twisted approximately another 180° in a clockwise direction about one another. Proximal tips of each of wires 242a and 242b are located relatively close to the positions they started at in FIG. 3a. Portions of each of wires 242a and 242b which are distal to the twist point between the two wires will typically not have moved relative to the locations they occupied at the state depicted in FIG. 3b, but could have depending upon how the associated tissue sampling device has been manipulated. Also shown in FIG. 3c is a cone Z which represents generally a 3-dimensional shape defined by the cutting paths of wires 242a and 242b, and corresponding roughly to a 3-dimensional shape of a sample of tissue cut from a tissue mass in a patient by transitioning wires 242a and 242b from the state shown in FIG. 3a to the state shown in FIG. 3c.

INDUSTRIAL APPLICABILITY

Figure 4:
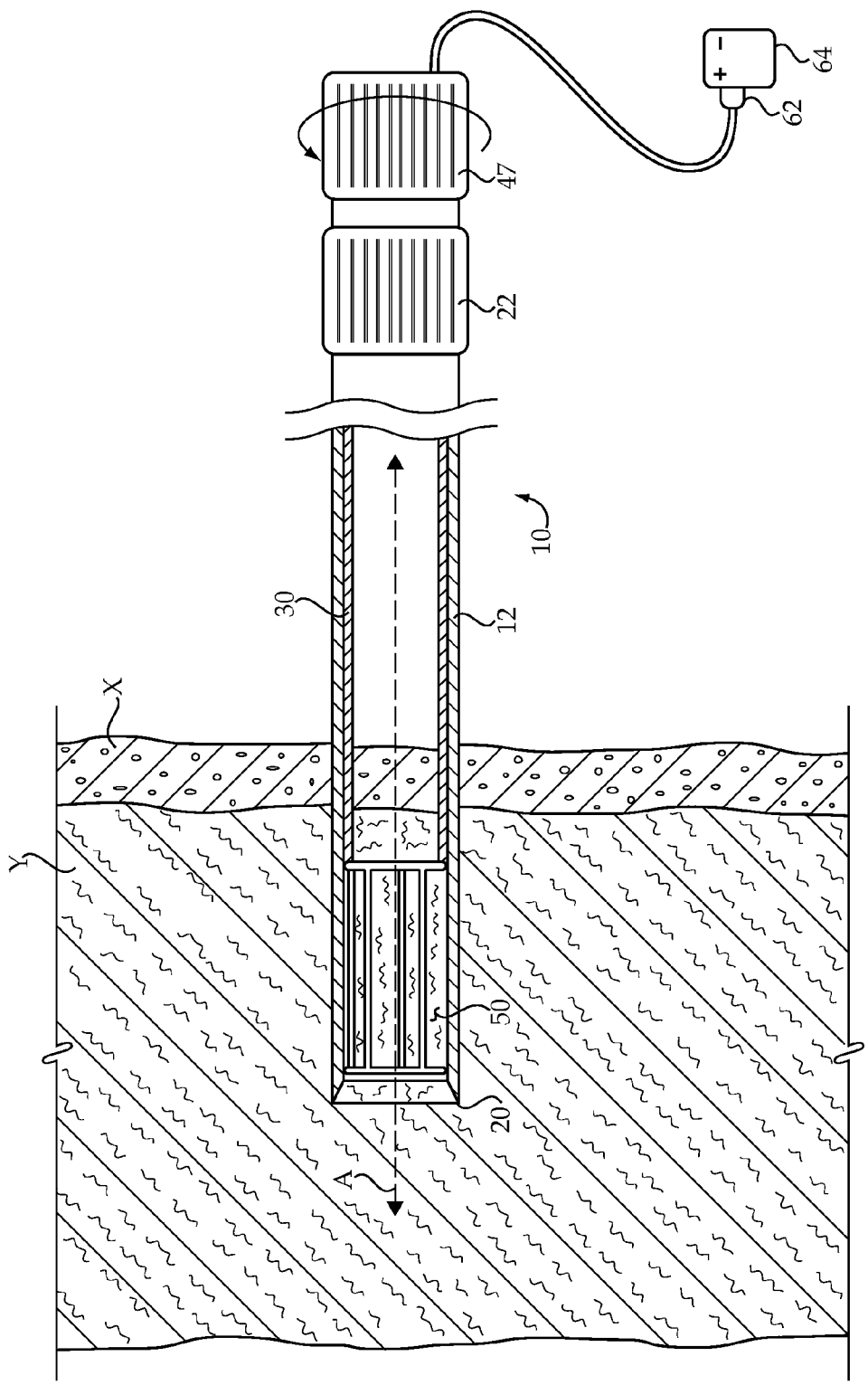
FIG. 4 is a partially sectioned side diagrammatic view of a tissue sampling device at one stage of a procedure for obtaining a sample of a body tissue.

Referring to the drawings generally, but in particular now to FIG. 4, there is shown device 10 as it might appear having been advanced through a skin layer X in a patient and into a mass of tissue such as muscle tissue Y. Adipose tissue (not shown) may be located between layers X and Y. A core of body tissue consisting of a piece of skin layer X and a piece of muscle tissue Y has been received within cannula 12 by way of advancing sharpened coring tip 20 into the patient. In particular, the still-attached core of body tissue is positioned within cavity 50. Electrical connector 62 is connected with electrical power source 64 such that an electrical current can pass through cutter 40 by way of electrically conductive material such as metallic material of shaft 30 and wires 42a-d. From the state shown in FIG. 4, handle 47 may be rotated relative to handle 22 to cause cutting mechanism 40 to actuate and detach the core of body tissue, or a portion thereof, received within cannula 12 and positioned within cavity 50.

Figure 5:
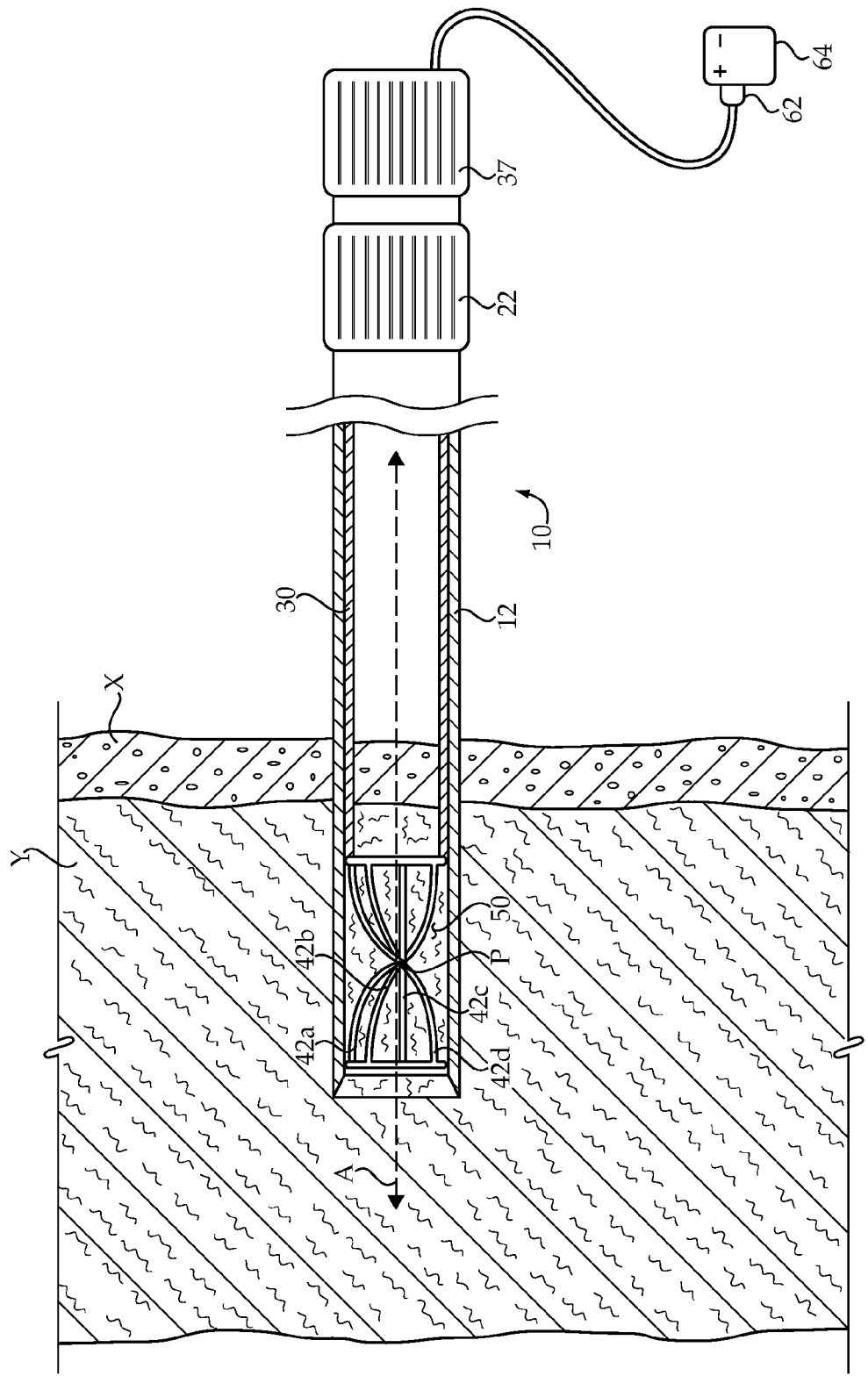
FIG. 5 is a partially sectioned side diagrammatic view of a tissue sampling device at another stage of obtaining a sample of body tissue.
Figure 6:
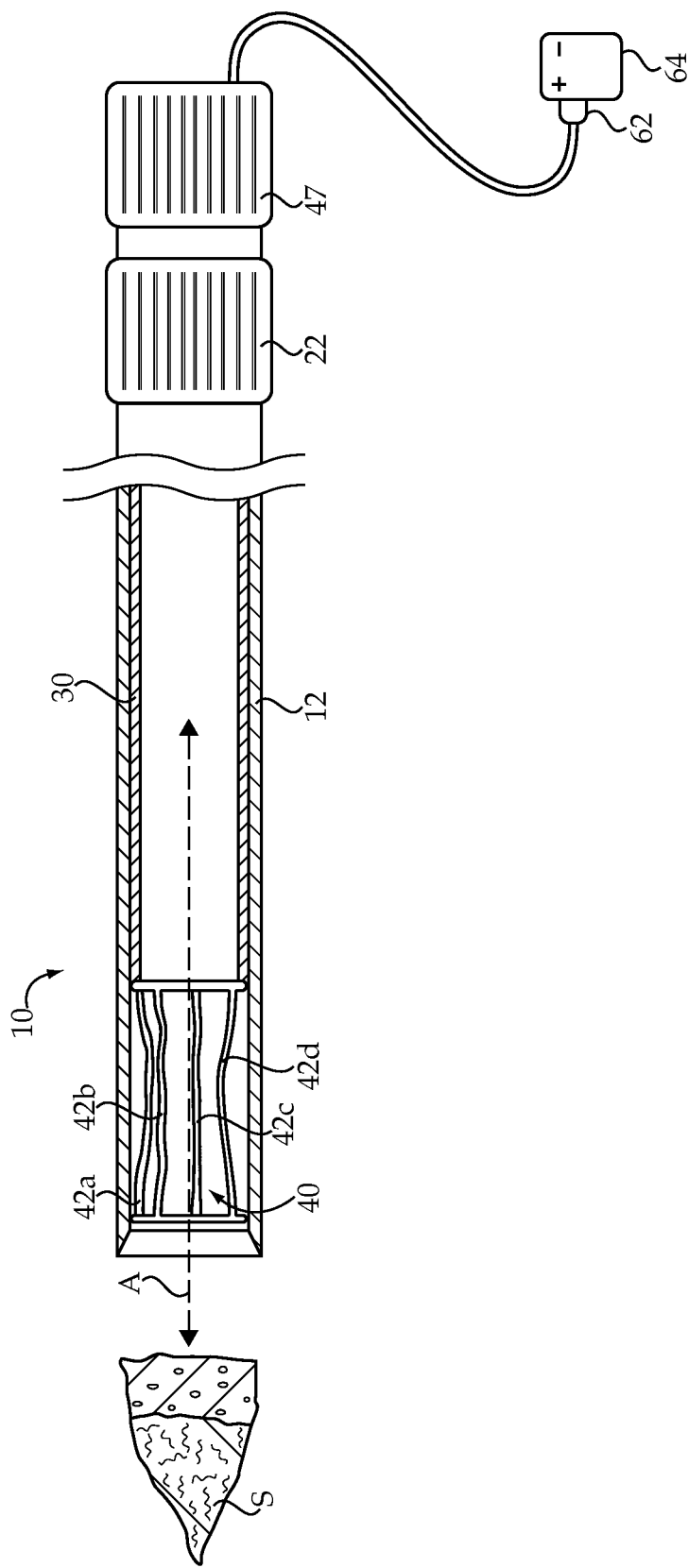
FIG. 6 is a partially sectioned side diagrammatic view of a tissue sampling device at yet another stage of obtaining a sample of body tissue.

Referring also now to FIG. 5, there is shown device 10 as it might appear where wires 42a-d have been twisted about one another at a twist point P intersected by longitudinal axis A, each having been swept through an arcing cutting path through the body tissue within cannula 12. As noted above, simultaneously sweeping multiple axially advancing wires in their respective arcing cutting paths through body tissue can effectively result in a compound cutting path defined by the intersection and/or overlap of the individual cutting paths of the separate wires 42a-d. Where multiple cutting wires are used, each sweeping through a cutting path defining a portion of a cone, the resulting compound cutting path may have a generally hyperboloid or hourglass shape as shown in FIG. 5. A hyberloid may include two conoids, hence a hyperboloid shape might also be considered conoidal. From the state shown in FIG. 5, device 10 may be withdrawn from the patient, removing the core of body tissue detached from the body tissue masses X and Y of the patient. The sample of body tissue removed may be that tissue which is positioned proximally of twist point P such that the twisted wires 42a-d capture the detached sample. Turning now to FIG. 6, when the detached body tissue is removed from the patient it will generally remain resident within device 10, as twisted wires 42a-d may entrap the detached tissue much like a basket or cage. To remove the sample, shown via reference letter S in FIG. 6, handle 47 may be counter-rotated relative to handle 22 to responsively untwist wires 42a-d. Tweezers or forceps may be used if needed to pull tissue sample S out of device 10. A vacuum, positive pressure, or still another technique might also be used to remove the detached sample.

As discussed above, device 10 may include a tissue admission configuration for admitting a core of body tissue into cannula 12, and may also include a second configuration or actuated configuration. As noted above, in the tissue admission configuration wires 42a-d may be generally linear in shape, and in the actuated configuration wires 42a-d may be plastically deformed to a curved shape. In other words, once wires 42a-d have been twisted about one another, some plastic deformation of wires 42a-d may occur such that wires 42a-d curve relative to longitudinal axis A rather than being strictly parallel. An "actuated" configuration could fairly be considered a state such as that shown in FIG. 5 at which wires 42a-d are twisted about one another, but could also fairly be considered a state such as that shown in FIG. 6 where wires 42a-d are untwisted but retain some curvature.

The present description is for illustrative purposes only, and should not be construed to narrow the breadth of the present disclosure in any way. Thus, those skilled in the art will appreciate that various modifications might be made to the presently disclosed embodiments without departing from the full and fair scope and spirit of the present disclosure. Other aspects, features and advantages will be apparent upon an examination of the attached drawings and appended claims.

What is claimed is:

1. A tissue sampling device comprising:
   a cannula including an elongate tubular body defining a longitudinal axis extending between a proximal cannula end and a distal cannula end having a sharpened coring tip;
   a shaft having a proximal shaft end, a distal shaft end, and being rotatably positioned within the cannula such that the distal shaft end is recessed from the sharpened coring tip; and
   a cutter having a plurality of axially advancing cutting elements extending within the cannula between the distal shaft end and the sharpened coring tip, the plurality of cutting elements each having a linear shape from a first cutting element end coupled to the distal shaft end to a second cutting element end coupled to the distal cannula end;
   each of the plurality of cutting elements further being movable in a different cutting path defining an arc about the longitudinal axis, responsive to rotating the shaft relative to the cannula to detach a piece of body tissue positioned within the cannula between the distal shaft end and the sharpened coring tip, and the different cutting paths intersecting at a point within the longitudinal axis.

2. The tissue sampling device of claim 1 wherein a cavity extends between the sharpened coring tip and the distal shaft end, and wherein each of the plurality of cutting elements includes an axially advancing wire having a first wire end coupled to the distal shaft end, a second wire end coupled to the distal cannula end, and being movable in the corresponding cutting path within the cavity.

3. The tissue sampling device of claim 2 wherein each of the plurality of axially advancing wires includes a segment of an electrical circuit, wherein the cannula further includes an electrically insulating coating, and further comprising an electrical connector electrically connected with the shaft.

4. The tissue sampling device of claim 2 wherein the cutting path defines a three-dimensional shape, and the arc is located on a surface of the three-dimensional shape.

5. The tissue sampling device of claim 2 wherein the three-dimensional shape includes a conoidal shape.

6. The tissue sampling device of claim 2 wherein a total number of the axially advancing wires is from two to five.

7. The tissue sampling device of claim 2 wherein the different cutting paths together define a hyperboloid shape.

8. The tissue sampling device of claim 2 wherein the plurality of axially advancing wires are oriented parallel the longitudinal axis and spaced at equal radial distances from the longitudinal axis, such that the axially advancing wires define a cylinder coaxial with the cannula.

9. The tissue sampling device of claim 8 wherein the cutter is in a tissue admission configuration, and is adjustable to a second configuration at which the plurality of axially advancing wires are twisted about one another within the cavity, responsive to rotating the shaft relative to the cannula.

10. A method of obtaining body tissue from a patient comprising the steps of:
    receiving the body tissue within a cannula defining a longitudinal axis, at least in part by advancing a sharpened coring tip of the cannula into a body tissue mass within the patient;
    rotating a shaft one full turn about the longitudinal axis relative to the cannula, where the shaft is positioned at an axial location within the cannula such that a tip of the shaft is recessed from the sharpened coring tip; and
    detaching a piece of the body tissue from the mass via sweeping a cutter having an axially advancing orientation in an arcing cutting path through the body tissue within the cannula, in response to the rotation of the shaft at the axial location.

11. The method of claim 10 wherein the step of detaching further includes simultaneously sweeping a plurality of axially advancing cutting wires in a plurality of arcing cutting paths through the body tissue within the cannula.

12. The method of claim 11 further comprising a step of capturing the piece of body tissue within the cannula at least in part by twisting the plurality of axially advancing cutting wires about one another.

13. The method of claim 12 further comprising a step of electrifying the plurality of axially advancing cutting wires during the step of detaching.

14. The method of claim 12 wherein the step of detaching further includes detaching a piece of muscle tissue from a muscle mass of the patient.

15. The method of claim 11 wherein the step of detaching further includes sweeping the plurality of axially advancing cutting wires in response to rotating the shaft, and the shaft extending within the cannula and being coupled to each of the axially advancing cutting wires.

16. A tissue sampling device comprising:
    a cannula defining a longitudinal axis, and having a sharpened coring tip;
    a shaft rotatably positioned within the cannula and recessed from the sharpened coring tip; and
    a cutter positioned within the cannula and having a plurality of axially advancing cutting wires extending within the cannula between the shaft and the sharpened coring tip;
    the cutter having a tissue admission configuration at which the axially advancing cutting wires each include a linear shape and are not in contact with one another, and an actuated configuration at which the axially advancing cutting wires each include a curved shape and are twisted together in contact with one another at a location between the shaft and the sharpened coring tip; and
    the cutter switching from the tissue admission configuration to the actuated configuration by rotating the shaft one complete turn relative to the cannula, and wherein the cutter is in the actuated configuration, and each of the axially advancing cutting wires is plastically deformed to the corresponding curved shape.

* * * * *